US006753529B2

(12) United States Patent
DiMarzio et al.

(10) Patent No.: US 6,753,529 B2
(45) Date of Patent: Jun. 22, 2004

(54) MULTIPLE WAVELENGTH MICROWAVE-ENHANCED INFRARED THERMOGRAPHY

(75) Inventors: Charles A. DiMarzio, Cambridge, MA (US); Carey M. Rappaport, Wellesley, MA (US); Taner Oktar, Boston, MA (US); Gerhard O. Sauermann, Lexington, MA (US)

(73) Assignee: Northeastern University, Boston, MA (US)

( * ) Notice: Subject to any disclaimer, the term of this patent is extended or adjusted under 35 U.S.C. 154(b) by 168 days.

(21) Appl. No.: 10/189,340

(22) Filed: Jul. 2, 2002

(65) Prior Publication Data

US 2003/0010919 A1 Jan. 16, 2003

Related U.S. Application Data

(60) Provisional application No. 60/302,874, filed on Jul. 3, 2001.

(51) Int. Cl.[7] .............................................. G01N 25/00
(52) U.S. Cl. .................................................. 250/341.6
(58) Field of Search ............................... 250/341.6, 347, 250/341.1

(56) References Cited

U.S. PATENT DOCUMENTS 6,343,534 B1 * 2/2002 Khanna et al. ............... 89/1.13
6,501,414 B2 * 12/2002 Arndt et al. .................. 342/22

FOREIGN PATENT DOCUMENTS

DE            40 30 802 A1 * 4/1992 ........... G01B/15/02
WO        WO 99/10731     3/1999 .......... G01N/21/71

OTHER PUBLICATIONS

L. J. Carter et al., "Landmine detection using stimulated infrared imaging," Geoscience and Remote Sensing Symposium, 2001. IGARSS '01. IEEE 2001 International, vol. 3, Jul. 9–13, 2001, pp. 1110–1112.*
S. I. Bragin et al., "Remote Detection of Objects in Soil Using a Microwave and IR Scanner," Microwave and Millimeter Wave Technology, 2000, 2nd International Conference on. ICMMT 2000, Sep. 14–16, 2000, pp. 607–610.*
L. J. Carter et al., "Thermal Imaging for Landmine Detection," Detection of Abandoned Land Mines, 1998. Second International Conference on the. IEE Conf. Publ. No. 458, Oct. 12–14, 1998, pp. 110–114.*

(List continued on next page.)

Primary Examiner—Constantine Hannaher
(74) Attorney, Agent, or Firm—Weingarten, Schurgin, Gagnebin & Lebovici LLP

(57) ABSTRACT

A microwave-enhanced infrared thermography technique for detecting buried objects exploits varying phase shifts experienced by different-frequency microwave signals reflected from objects back toward the surface, the phase shifts resulting in different interference patterns and therefore different temperature distribution patterns near the surface. Respective infrared images of an area are captured prior to microwave heating, after a first heating with a first frequency, and after heating with a second frequency different from the first. Pairs of the images are subtracted to form temperature rise images showing patterns of temperature rise in the two cycles, and the temperature rise images are subtracted to form a difference image which is analyzed to identify characteristics indicating the presence of buried objects.

6 Claims, 2 Drawing Sheets

OTHER PUBLICATIONS

DiMarzio et al., "Some Approaches to Infrared Spectroscopy for Detection of Buried Objects", Detection and Remediation Technologies for Mines and Minelike Targets III., Proc., SPIE vol. 3392, p. 158–166, Sep. 1998.

DiMarzio et al., "Microwave–Enhanced Infrared Thermography", Detection and Remediation Technologies for Mines and Minelike Targets III., Proc., SPIE vol. 3392, p. 1103–1110, Sep. 1998.

DiMarzio et al., " Microwave–Enhanced Infrared Thermography", Environmental Monitoring and Remediation Technologies, Proc., SPIE vol. 3534, p. 337–342, Feb. 1999.

DiMarzio et al., " Microwave–Enhanced Infrared Thermography", Detection and Remediation Technologies for Mines and Minelike Targets IV, Proc., SPIE vol. 3710, p. 173–179, Aug. 1999.

DiMarzio et al, "Detection of Objects Buried in Soil Using Microwave Heating", Environmental Monitoring and Remediation Technologies II, Proc., SPIE vol. 3853, p. 311–320, Dec. 1999.

DiMarzio et al, "Effects of Surface Roughness on Microwave Heating of Soil for Detection of Buried Land Mines", Detection and Remediation Technologies for Mines and Minelike Targets V, Proc., SPIE vol. 4038, p. 200–208, Aug. 2000.

* cited by examiner

MULTIPLE WAVELENGTH MICROWAVE-ENHANCED INFRARED THERMOGRAPHY

CROSS REFERENCE TO RELATED APPLICATIONS

This application claims priority under 35 U.S.C. §119(e) of provisional patent application serial No. 60/302,874 filed Jul. 3, 2001.

STATEMENT REGARDING FEDERALLY SPONSORED RESEARCH OR DEVELOPMENT

Partial funding under U.S. Department of Defense contract No. DAAG55-97-1-0013 was provided for the development of the invention disclosed herein.

BACKGROUND OF THE INVENTION

There is a need to detect, locate and identify underground or buried objects such as mines, buried waste and utility structures. Existing techniques for detecting, locating and identifying underground objects include techniques employing ground-penetrating radar and solar thermal imaging. While ground-penetrating radar has proven to be useful in detecting underground objects, it suffers from limited resolution, which makes the locating and identification of underground objects difficult. Solar thermal imaging, which utilizes thermal images from solar heating of the ground, is limited in that sunlight does not penetrate the ground to any appreciable depth, and it can only be used during certain hours when sunlight levels are changing. Further, the captured image is somewhat weak, because it is produced entirely by heat transfer, and is noisy due to uneven absorption of sunlight at the surface.

Recently, the use of microwave-enhanced thermal imaging, or thermography, has been proposed for use in locating buried objects such as land mines. Generally, microwave-enhanced thermography involves directing a high-energy microwave signal onto the surface of an area of interest from an aerially suspended microwave antenna, and utilizing an infrared camera to capture an image of the resulting heating. This image is compared with an infrared image of the same area prior to such microwave heating, and the difference between the images is analyzed for indications of buried objects. This technique relies on the reflection of the microwave signal from the object back toward the surface and the resulting pattern of interference with the incident microwave signal. When the heating cycle is of the proper duration, the interference pattern can be detected by the infrared camera as a corresponding temperature distribution on the surface. The benefits of microwave-enhanced thermography include relatively high resolution, control over the heating cycle, and speed of analysis.

It has been noted that the microwave-enhanced thermography technique as described above can work well when the surface is relatively smooth, but its performance suffers if the surface has appreciable irregularity or roughness. It is believed that this degraded performance arises from distortions in the microwave field caused by the irregularities, resulting in variations in the heating of the ground that are greater than those associated with the buried object(s). This effect has been referred to as "noise" or "clutter" induced by surface roughness. If this noise is sufficiently high, it becomes much more difficult to reliably detect signal features caused by a buried object, resulting in missed detections and false alarms.

It would be desirable to enable microwave-enhanced thermography to be used in areas having appreciable surface roughness without the degraded performance that has heretofore been observed.

BRIEF SUMMARY OF THE INVENTION

In accordance with the present invention, technique for performing microwave-enhanced infrared thermography is disclosed that performs well even in the presence of surface roughness.

The disclosed technique is based on the observation that the heating of the surface area is primarily dependent upon the field strength at the surface, which is substantially independent of the frequency of the microwave energy. However, the pattern of mixing of the reflected field from a buried object with the incident field varies with frequency, due to differences in the relative phase shifts caused by the propagation of the signals from the surface down to the object and back to the surface. These different mixing patterns induce corresponding different temperature patterns on the surface, which are subtracted. The result is a difference image with reduced noise from surface roughness due to the canceling effect of the subtraction.

Thus, in the disclosed thermography method, a first infrared image of a target surface area of interest is captured prior to any microwave heating. Then the target area is heated using microwaves of a first frequency, and a first "heated" infrared image is captured. These two images are subtracted to form a first "temperature rise" image showing a pattern of temperature rise on the surface as a result of this first heating cycle.

Subsequently, the target area is heated using a different microwave frequency, and a second heated infrared image is captured. The second heated infrared image is used in calculating a second temperature rise image. The first temperature rise image from the first heating cycle is subtracted from the second temperature rise image of the second heating cycle, and the difference image is subject to image analysis to identify any characteristics indicating the presence of a buried object in the target area. The microwave signals have respective frequencies that are suitably widely spaced to maximize the difference in phase shifts and therefore the interference patterns of the two heating cycles, to yield an acceptably high signal-to-noise ratio in the difference image.

Other aspects, features, and advantages of the present invention will be apparent from the detailed description that follows.

BRIEF DESCRIPTION OF THE SEVERAL VIEWS OF THE DRAWINGS

The invention will be more fully understood by reference to the following Detailed Description of the Invention in conjunction with the Drawing, of which.

DETAILED DESCRIPTION OF THE INVENTION

The disclosure of provisional patent application serial No. 60/302,874 filed Jul. 3, 2001 is incorporated herein by reference.

Figure 1:
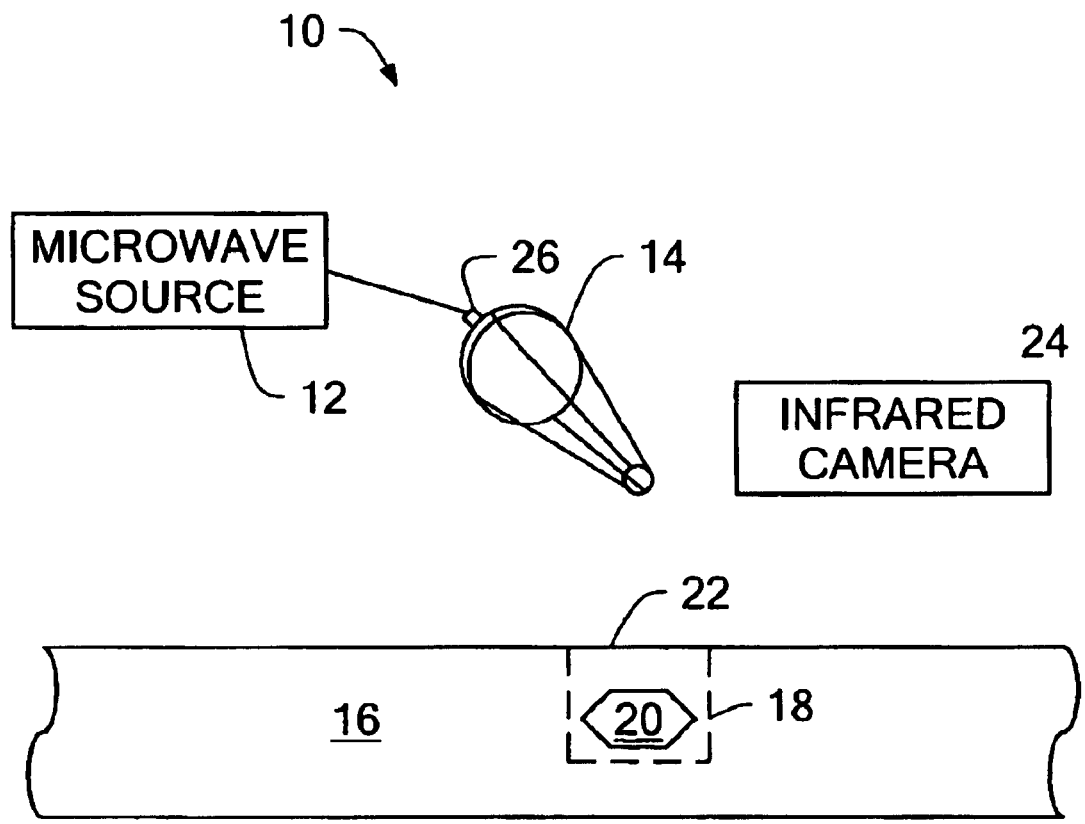
FIG. 1 is a diagram of an apparatus for detecting and identifying underground objects utilizing microwave enhanced infrared thermography in accordance with the present invention.

Referring to FIG. 1, an apparatus 10 for detecting underground devices utilizing multiple wavelength microwave-enhanced infrared thermography is shown. The apparatus 10 includes a microwave source 12 in communication with an antenna 14 which couples microwaves generated by the microwave source 12 to the ground 16. The microwaves penetrate a target area 18 of the ground 16, which may include objects 20 to be detected. The frequencies of the microwaves provided by the microwave source 12 are selected according to the expected depth of the objects 20 and/or the soil conditions, such that the microwaves heat the ground area 18 at a pre-selected depth from the surface 22. As explained in more detail below, a distribution of different temperatures is produced on the surface 22 above the object 20, and a recording device such as an infrared camera 24 is used to capture an image of this temperature distribution. The image from the infrared camera 24 is provided to an image processing system (not shown).

The antenna 14 in a preferred embodiment comprises an elliptical reflector antenna oriented with respect to the ground at a pseudo-Brewster angle to produce a transverse-magnetically (TM) polarized microwave beam. The pseudo-Brewster angle is the angle at which the maximum amount of power is coupled from air into soil, and almost all of the radiated microwave energy is used in heating the soil, with a minimal amount reflected back towards the air. The pseudo-Brewster angle varies with soil type, density and moisture content. For common variations in soil characteristics, the pseudo-Brewster angle tends to be greater than sixty degrees and less than eighty degrees.

The antenna 14 is mounted above the ground 16, with a feed 26 from the microwave source 12 at one focal point and the target ground area 18 at another focal point, and with its major axis (the line intersecting the two focal points) aligned at the pseudo-Brewster angle with respect to the surface 22 of the ground 16. For a given antenna height h above the ground, the target area 18 is therefore about 2 h to 5.6 h forward of the antenna. The converging rays from all parts of the elliptical reflector antenna 14 arrive at the target focal point with a range of angles. As long as the major axis of the antenna is close to the pseudo-Brewster angle corresponding to the average soil characteristics of the area being examined, many of the rays are incident on the ground surface 22 with nearly optimal orientation, despite small local variations in soil type. The utilization of the elliptical reflector antenna 14 thus provides power concentration and ensures that most of the power enters the soil, despite soil conditions which change with position, and does so for target areas 18 in front of the antenna 14.

The system of FIG. 1 works on the principle of wave interference. The incident plane wave from the antenna 14 travels downward into the ground 16, and the portion of this wave that encounters an object 20 is reflected back toward the surface 22. This reflected wave mixes with the incident wave in a pattern of constructive and destructive interference in the soil above the object 20. This interference pattern, in turn, results in a corresponding pattern of heating, or temperature rise, on the surface area 22 of the soil. This pattern can be detected by the infrared camera 24.

Prior microwave-enhanced infrared thermography techniques have utilized one heating cycle. A first infrared image is captured prior to the heating cycle to represent the pattern of background infrared energy in the area of interest. Then the microwave source 12 is activated, a predetermined amount of time is permitted to elapse for heating the area 18, and a second infrared image is then captured. The first image is subtracted from the second image to substantially remove the contribution of the background infrared energy, leaving the pattern of infrared energy resulting from the microwave heating alone. This difference image is processed to identify any characteristics that may indicate the presence of an object 20 under the surface 22.

As mentioned above, the prior technique has degraded performance when the surface 22 exhibits too much roughness. For that reason, the presently disclosed technique includes features that reduce the effect of such surface roughness on the quality of the resulting infrared image. Specifically, two separate heating cycles using different microwave frequencies are utilized, the respective infrared images from these two heating cycles are subtracted, and the resulting difference image is analyzed to ascertain the presence or absence of buried objects 20. The effectiveness of such a technique can be explained as follows. The heating, at least for short times, is primarily dependent upon the field strength at the surface 22, which is substantially independent of the frequency of the microwave energy (at least over a suitably small frequency range). However, the pattern of mixing of the reflected field from the buried object 20 with the incident field varies with frequency. This variation is due to the respective phase shifts of the reflected microwave signals caused by the propagation of the signals from the surface 22 to the object 20 and back to the surface 22. The constant propagation delay results in a phase shift of one value at one frequency, but a phase shift of a different value at a different frequency. These different phase shifts result in different interference patterns and corresponding different temperature distributions on the surface 22, which can be detected by the infrared camera 24.

Figure 2:
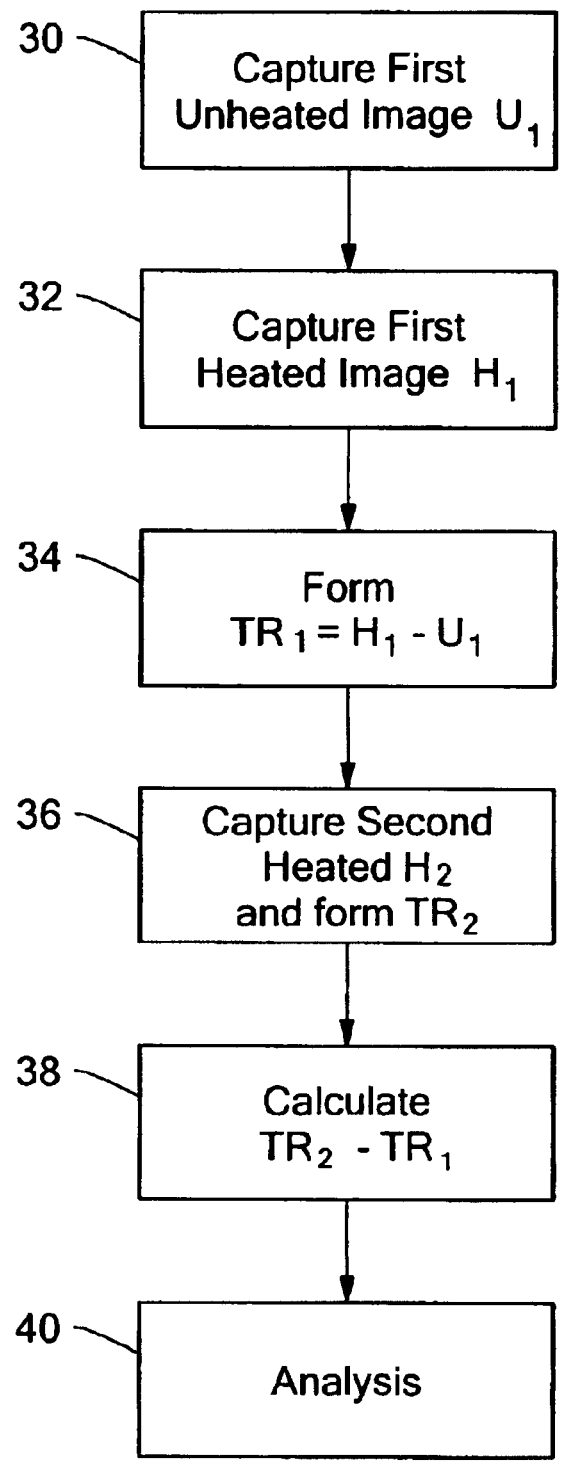
FIG. 2 is a flow chart of a method for detecting and identifying underground objects utilizing multiple wavelength microwave-enhanced infrared thermography in accordance with the present invention.

FIG. 2 shows a specific embodiment of the process. At step 30, an initial infrared image $U_1$ of the surface 22 is captured prior to any microwave heating. Then at step 32, the target area 18 is heated using microwaves of a first frequency, and a first "heated" infrared image $H_1$ is captured. At step 34, the image $U_1$ is subtracted from the image $H_1$ to form a first temperature rise image $TR_1$ showing a pattern of temperature rise on the surface 22 as a result of the first heating cycle.

At step 36, a second heating cycle is executed using a different microwave frequency, and a second heated image $H_2$ is captured. It is preferred that the second heating take place substantially immediately after the first heating cycle, in which case the second temperature rise image $TR_2$ is formed as the difference between the second heated image $H_2$ and the first heated image $H_1$. If for some reason there is appreciable delay between the two heating cycles, it may be necessary to capture a second initial image at the beginning of the second heating cycle, rather than simply using the first heated image $H_1$ as the initial image, because the temperature distribution will likely have changed due to thermal diffusion between the end of the first heating cycle and the beginning of the second. In such a case, the second temperature rise image $TR_2$ is formed as the difference between the second heated image $H_2$ and such second initial image.

At step 38, the first temperature rise image $TR_1$ is subtracted from the second temperature rise image $TR_2$. This difference image is subject to image analysis at step 40 to identify any characteristics indicating the presence of an object 20.

It will be appreciated that it is desirable to employ microwave signals whose respective frequencies are widely spaced so as to maximize the difference in phase shifts and therefore the interference patterns of the two heating cycles, to yield an acceptably high signal-to-noise ratio in the difference image $TR_2$-$TR_1$. This is important for reliable operation, that is, acceptably high probabilities of correct detections and acceptably low probabilities of false alarms. However, the signals should not be so widely spaced that the fundamental assumptions of the model break down, including the assumption of equal incident field strength near the surface 22 for both heating cycles and the assumption of constant propagation and reflection properties of the target area 18 and object 20. The selection of good frequency pairs can be made based on the characteristics of the soil, the expected depth and size of the objects 20, and the degree of roughness of the surface 22, among other considerations.

While the foregoing has shown the use of two frequencies and two heating cycles, it will be appreciated that in alternative embodiments it may be beneficial to capture more than two heated images, using either the same frequencies or additional frequencies.

It will be apparent to those skilled in the art that modifications to and variations of the disclosed methods and apparatus are possible without departing from the inventive concepts disclosed herein, and therefore the invention should not be viewed as limited except to the full scope and spirit of the appended claims.

What is claimed is:

1. A method for detecting whether an object is buried beneath a target surface area of the ground, comprising:
    1) in a first cycle:
        a) capturing a first infrared image of the target surface area indicative of a first initial temperature distribution thereon;
        b) directing a microwave signal of a first frequency at the target surface area and capturing a second infrared image of the target surface area indicative of a first heated temperature distribution thereon; and
        c) subtracting the first infrared image from the second infrared image to form a first temperature rise image;
    2) in a second cycle:
        a) directing a microwave signal of a second frequency at the target surface area and capturing a third infrared image of the target surface area indicative of a second heated temperature distribution thereon, the second frequency differing from the first frequency by an amount effective to yield an acceptably high signal to noise ratio in a difference image to be calculated as part of the method; and
        b) subtracting a fourth infrared image from the third infrared image to form a second temperature rise image, the fourth infrared image being indicative of a second initial temperature distribution of the target surface area at the beginning of the second cycle; and
    3) subtracting the first temperature rise image from the second temperature rise image to obtain the difference image for processing to identify characteristics indicative of the presence of a buried object.

2. A method according to claim 1, wherein the first initial temperature distribution is a background temperature distribution existing prior to any microwave heating of the target surface area.

3. A method according to claim 1, wherein the second cycle is performed substantially immediately after the first cycle such that the second initial temperature distribution is substantially the first heated temperature distribution, and wherein the fourth infrared image used to calculate the second temperature rise image is the second infrared image captured in the first cycle.

4. A method according to claim 1, wherein the second cycle is performed sufficiently after the first cycle that thermal diffusion may cause the second initial temperature distribution to differ from the first heated temperature distribution, and further comprising capturing the fourth infrared image used to calculate the second temperature rise image at the beginning of the second cycle.

5. A method according to claim 1, further comprising one or more additional cycles, each additional cycle including (i) directing a respective microwave signal at the target surface area, (ii) capturing a respective heated infrared image of the target surface area indicative of a respective heated temperature distribution thereon, and (iii) subtracting a respective initial infrared image from the respective heated infrared image to form a respective temperature rise image, each initial infrared image being indicative of a respective initial temperature distribution on the surface of the target area, and further comprising using the additional temperature rise images in the calculation of the difference image.

6. A method according to claim 5, wherein each of the additional cycles uses a respective microwave frequency different from the respective microwave frequencies used in the other cycles.

* * * * *